United States Patent [19]

Terada et al.

[11] Patent Number: 4,989,983
[45] Date of Patent: Feb. 5, 1991

[54] TEST SAMPLE COLOR COMPARISON DEVICE

[75] Inventors: Takao Terada; Hiroyuki Ota, both of Osaka; Shigeru Makita, Kyoto, all of Japan

[73] Assignee: Omron Corporation, Kyoto, Japan

[21] Appl. No.: 461,530

[22] Filed: Jan. 5, 1990

Related U.S. Application Data

[62] Division of Ser. No. 268,561, Nov. 8, 1988.

[30] Foreign Application Priority Data

Nov. 9, 1987 [JP] Japan .................................. 62-282780
Dec. 7, 1987 [JP] Japan .................................. 62-310246

[51] Int. Cl.[5] ........................................................ G01J 3/52
[52] U.S. Cl. .................................... 356/423; 364/413.09
[58] Field of Search ................ 356/421, 422, 423, 424; 364/413.09, 413.11, 526

[56] References Cited

U.S. PATENT DOCUMENTS 2,058,072 10/1936 Fritzching .
4,871,258 10/1989 Herpichboehm et al. .......... 356/422

FOREIGN PATENT DOCUMENTS

2129 of 1909 United Kingdom .

Primary Examiner—F. L. Evans
Attorney, Agent, or Firm—Dickstein, Shapiro & Morin

[57] ABSTRACT

A test sample color comparison device is disclosed which has a casing unit with an insertion slot for inserting a color test sample therein, and a display section for displaying the color test sample adjacent at least one of a plurality of reference color shades, as the reference color shades are successively moved into position adjacent the color test sample by a manipulation wheel. When an operator determines that a reference color shade adjacent the test sample corresponds in color to the color of the test sample, he pushes a switch to cause a readout of stored information corresponding to the reference color shade then adjacent the test sample. Readout of the stored information is based on a bit pattern set by a plurality of converter switches which are turened on and off in different patterns which correspond to the different color shades as the reference color shades are moved into position by the manipulation wheel. An uneven pattern code section moves in association with the manipulatable wheel and actuates the converter switches. A preferred uneven pattern code section is arranged so that all of the converter switches are actuated roughly equally during a full rotation of the manipulatable wheel, and so that only one of the converter switches is switched on or off during incremental movement of the manipulable wheel.

7 Claims, 13 Drawing Sheets

|  | BIT 4 | BIT 3 | BIT 2 | BIT 1 | 16 STAGES |
|---|---|---|---|---|---|
| ① | 0 | 0 | 0 | 1 | = 1 |
| INTERIM | 0 | 0 | 1 | 0 | = 2 |
| ② | 0 | 0 | 1 | 1 | = 3 |
| INTERIM | 0 | 1 | 0 | 0 | = 4 |
| ③ | 0 | 1 | 0 | 1 | = 5 |
| INTERIM | 0 | 1 | 1 | 0 | = 6 |
| ④ | 0 | 1 | 1 | 1 | = 7 |
| INTERIM | 1 | 0 | 0 | 0 | = 8 |
| ⑤ | 1 | 0 | 0 | 1 | = 9 |
| INTERIM | 1 | 0 | 1 | 0 | = A |
| ⑥ | 1 | 0 | 1 | 1 | = B |
| INTERIM | 1 | 1 | 0 | 0 | = C |
| ⑦ | 1 | 1 | 0 | 1 | = D |
| INTERIM | 1 | 1 | 1 | 0 | = E |
| ⑧ | 1 | 1 | 1 | 1 | = F |
| INTERIM | 0 | 0 | 0 | 0 | = 0 |
| SWITCHING NO. | 1 | 3 | 7 | 15 | |

FIG. 8

|  | BIT 4 | BIT 3 | BIT 2 | BIT 1 | 16 STAGES |
|---|---|---|---|---|---|
| ① INTERIM | 0 | 0 | 0 | 0 | = 0 |
| ② INTERIM | 0 | 0 | 0 | 1 | = 1 |
| ③ INTERIM | 0 | 1 | 0 | 1 | = 5 |
| ④ INTERIM | 0 | 1 | 1 | 1 | = 7 |
| ⑤ INTERIM | 0 | 1 | 1 | 0 | = 6 |
| ⑥ INTERIM | 1 | 0 | 0 | 0 | = 4 |
| ⑦ INTERIM | 1 | 1 | 0 | 0 | = C |
| ⑧ INTERIM | 1 | 0 | 0 | 0 | = 8 |
| | 1 | 0 | 0 | 1 | = 9 |
| | 1 | 0 | 1 | 1 | = B |
| | 0 | 0 | 1 | 1 | = 3 |
| | 0 | 0 | 1 | 0 | = 2 |
| | 1 | 1 | 1 | 0 | = A |
| | 1 | 1 | 1 | 1 | = E |
| | 1 | 1 | 0 | 1 | = F |
| | 1 | 1 | 0 | 1 | = D |
| SWITCHING NO. | 3 | 3 | 4 | 5 | ---5 |

FIG. 11

|  | BIT 4 | BIT 3 | BIT 2 | BIT 1 | 16 STAGES |
|---|---|---|---|---|---|
| ① INTERIM | 0 | 0 | 0 | 0 | = 0 |
| ② INTERIM | 0 | 0 | 1 | 0 | = 2 |
| ③ INTERIM | 0 | 1 | 1 | 0 | = 6 |
| ④ INTERIM | 0 | 1 | 1 | 1 | = 7 |
| ⑤ INTERIM | 0 | 1 | 0 | 1 | = 5 |
| ⑥ INTERIM | 0 | 1 | 0 | 0 | = 4 |
| ⑦ INTERIM | 1 | 1 | 0 | 0 | = C |
| ⑧ INTERIM | 1 | 0 | 0 | 0 | = 8 |
| | 1 | 0 | 1 | 0 | = A |
| | 1 | 0 | 1 | 1 | = B |
| | 0 | 0 | 1 | 1 | = 3 |
| | 0 | 0 | 0 | 1 | = 1 |
| | 1 | 0 | 0 | 1 | = 9 |
| | 1 | 1 | 0 | 1 | = D |
| | 1 | 1 | 1 | 0 | = F |
| | 1 | 1 | 1 | 0 | = E |
| SWITCHING NO. | 3 | 3 | 5 | 4 | ---5 |

| | BIT 4 | BIT 3 | BIT 2 | BIT 1 | | 16 STAGES |
|---|---|---|---|---|---|---|
| ① | 0 | 0 | 0 | 0 | = | 0 |
| INTERIM ② | 0 | 1 | 0 | 0 | = | 4 |
| INTERIM ③ | 0 | 1 | 1 | 0 | = | 6 |
| INTERIM ④ | 0 | 1 | 1 | 1 | = | 7 |
| INTERIM ⑤ | 0 | 0 | 1 | 1 | = | 3 |
| INTERIM ⑥ | 0 | 0 | 1 | 0 | = | 2 |
| INTERIM ⑦ | 1 | 0 | 1 | 0 | = | A |
| INTERIM ⑧ | 1 | 0 | 0 | 0 | = | 8 |
| INTERIM | 1 | 1 | 0 | 0 | = | C |
| INTERIM | 1 | 1 | 0 | 1 | = | D |
| | 0 | 1 | 0 | 1 | = | 5 |
| | 0 | 0 | 0 | 1 | = | 1 |
| | 1 | 0 | 0 | 1 | = | 9 |
| | 1 | 1 | 1 | 1 | = | B |
| | 1 | 1 | 1 | 1 | = | F |
| | 1 | 1 | 1 | 0 | = | E |
| SWITCHING NO. | 3 | 5 | 3 | 4---5 | | |

FIG. 13

| | BIT 4 | BIT 3 | BIT 2 | BIT 1 | | 16 STAGES |
|---|---|---|---|---|---|---|
| ① | 0 | 0 | 0 | 0 | = | 0 |
| INTERIM ② | 0 | 1 | 0 | 0 | = | 4 |
| INTERIM ③ | 0 | 1 | 0 | 1 | = | 5 |
| INTERIM ④ | 0 | 1 | 1 | 1 | = | 7 |
| INTERIM ⑤ | 0 | 0 | 1 | 1 | = | 3 |
| INTERIM ⑥ | 0 | 0 | 0 | 1 | = | 1 |
| INTERIM ⑦ | 1 | 0 | 0 | 1 | = | 9 |
| INTERIM ⑧ | 1 | 0 | 0 | 0 | = | 8 |
| INTERIM | 1 | 1 | 0 | 0 | = | C |
| INTERIM | 1 | 1 | 1 | 0 | = | E |
| | 0 | 1 | 1 | 0 | = | 6 |
| | 0 | 0 | 1 | 0 | = | 2 |
| | 1 | 0 | 1 | 0 | = | A |
| | 1 | 1 | 1 | 1 | = | B |
| | 1 | 1 | 1 | 1 | = | F |
| | 1 | 1 | 0 | 1 | = | D |
| SWITCHING NO. | 3 | 5 | 4 | 3---5 | | |

|   | BIT 5 | BIT 4 | BIT 3 | BIT 2 | BIT 1 |   | 32 STAGES |
|---|---|---|---|---|---|---|---|
| ① | 1 | 1 | 1 | 1 | 0 | = | 30 |
| ② | 1 | 1 | 1 | 1 | 1 | = | 31 |
| ③ | 1 | 1 | 0 | 1 | 1 | = | 27 |
|   | 1 | 1 | 0 | 0 | 1 | = | 25 |
|   | 1 | 0 | 0 | 0 | 1 | = | 17 |
|   | 1 | 0 | 1 | 0 | 1 | = | 21 |
|   | 1 | 1 | 1 | 0 | 1 | = | 29 |
|   | 1 | 1 | 1 | 0 | 0 | = | 28 |
|   | 1 | 1 | 0 | 0 | 0 | = | 24 |
|   | 1 | 1 | 0 | 1 | 0 | = | 26 |
|   | 1 | 0 | 0 | 1 | 0 | = | 18 |
|   | 1 | 0 | 0 | 1 | 1 | = | 19 |
|   | 1 | 0 | 1 | 1 | 1 | = | 23 |
|   | 1 | 0 | 1 | 1 | 0 | = | 22 |
|   | 1 | 0 | 1 | 0 | 0 | = | 20 |
|   | 1 | 0 | 0 | 0 | 0 | = | 16 |
|   | 0 | 0 | 0 | 0 | 0 | = | 0 |
|   | 0 | 0 | 0 | 0 | 1 | = | 1 |
|   | 0 | 0 | 1 | 0 | 1 | = | 5 |
|   | 0 | 0 | 1 | 1 | 1 | = | 7 |
|   | 0 | 0 | 1 | 1 | 0 | = | 6 |
|   | 0 | 0 | 1 | 0 | 0 | = | 4 |
|   | 0 | 1 | 1 | 0 | 0 | = | C |
|   | 0 | 1 | 0 | 0 | 0 | = | 8 |
|   | 0 | 1 | 0 | 0 | 1 | = | 9 |
|   | 0 | 1 | 0 | 1 | 1 | = | B |
|   | 0 | 0 | 0 | 1 | 1 | = | 3 |
|   | 0 | 0 | 0 | 1 | 0 | = | 2 |
|   | 0 | 1 | 0 | 1 | 0 | = | A |
|   | 0 | 1 | 1 | 1 | 0 | = | E |
|   | 0 | 1 | 1 | 1 | 1 | = | F |
| ㉜ | 0 | 1 | 1 | 0 | 1 | = | D |
| SWITCHING NO. | 1 | 6 | 8 | 7 | 9 |   |   |

TEST SAMPLE COLOR COMPARISON DEVICE

This is a division of application Ser. No. 268,561, filed Nov. 8, 1988.

BACKGROUND OF THE INVENTION (A) Field of the Invention

This invention relates to a test sample color comparison device used in biochemical examinations (urine sugar, blood sugar, urobilin and other such examinations), for example, the invention relates to a test sample color comparison device used to determine the amount of sugar present in urine by comparing the color of portion of a test paper treated with a reagent and wetted by urine with a plurality of reference color shades representing different levels of urine sugar.

(B) Brief Discussion of the Prior Art

Figure 5:
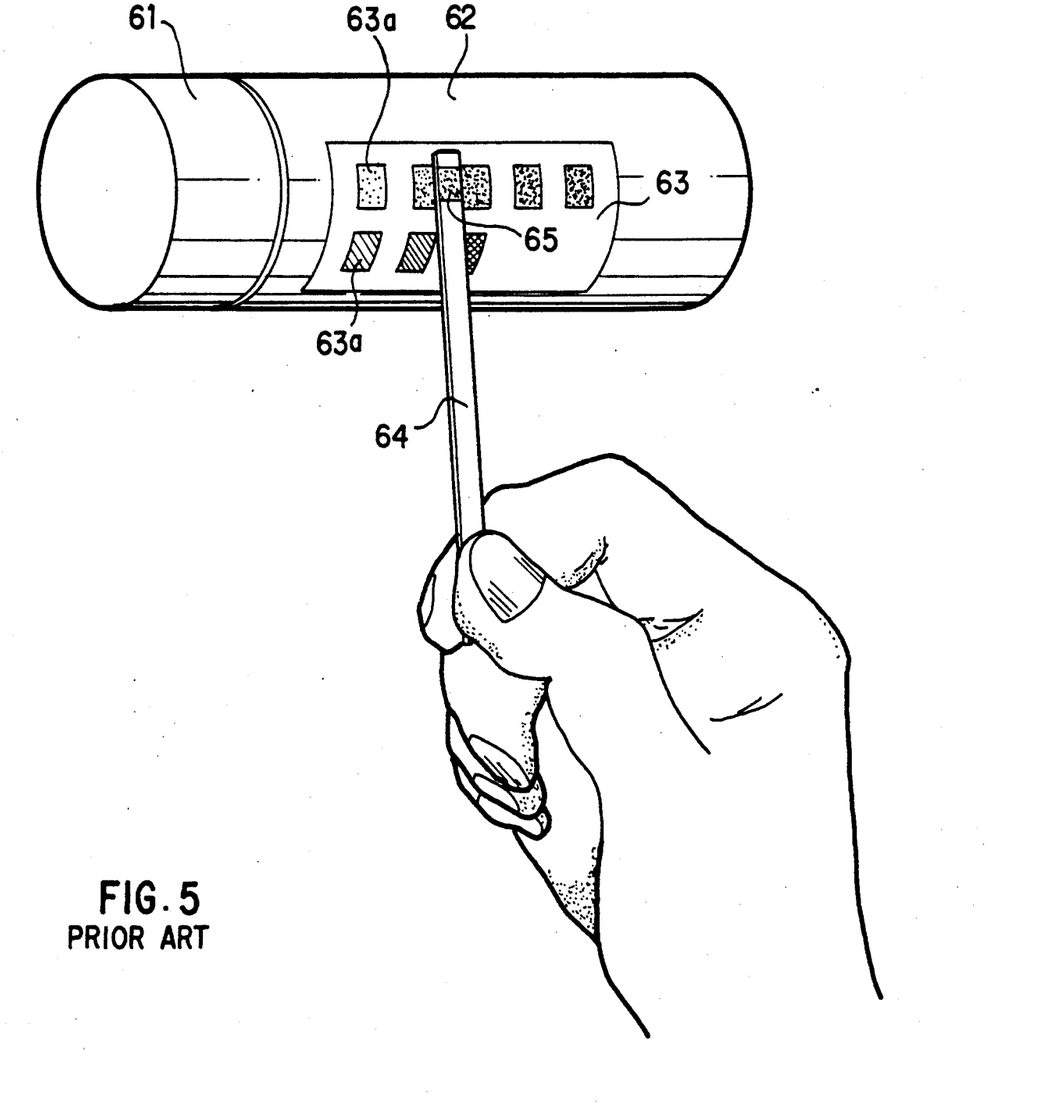
FIG. 5 shows a prior art comparison device.

FIG. 5 illustrates a prior art test sample color comparison device. It is constructed of a cylindrical case 62, equipped with a cap section 61, on which a color sample sheet 63 used for a color comparison is attached. The cylindrical case contains, for example, test sticks 64 used in urine sugar examinations. Test stick 64 is a resin sheet having a test paper 65 which has been soaked in a reagent attached to one end. When conducting a urine sugar examination, cap 61 is removed, a test stick 64 is removed from the cylindrical case, and test paper 65 is wetted with urine. The urine wetted test stick 65 displays various color reactions in response to the sugar level in the urine. The resultant color appearing on test paper 65 is compared with the color sample 63 provided for comparative purposes on cylindrical case 62 to determine a color which best matches the color of test paper 65 thereby giving an indication of the urine sugar level. That is, the various colors 63a (colors indicating positive and negative sugar results) which result according the level of sugar in the urine (glucose) are arrayed on color sample sheet 63. By comparing the color of the test sample paper 65 with the various colors 63a on the color sample sheet a determination of the level of sugar in the urine can be made by finding the same or approximately the same color.

Because the color sample sheet 63 is attached to the outside of the cylindrical case 62 which holds the test sticks, the test paper 65 wetted with urine must be held close to the color samples 63a for comparison with each. In other words during the process of color comparison, it is necessary for one to hold the urine wetted test paper so that it does not come in contact with the color samples, but yet move the test sample from color to color. This requires special diligence an dexterity on the part of the person making the comparison making it easy to misalign the test sample paper with the color sample to be compared, and having the disadvantage that it is difficult to accurately determine slight color differences.

Figure 6:
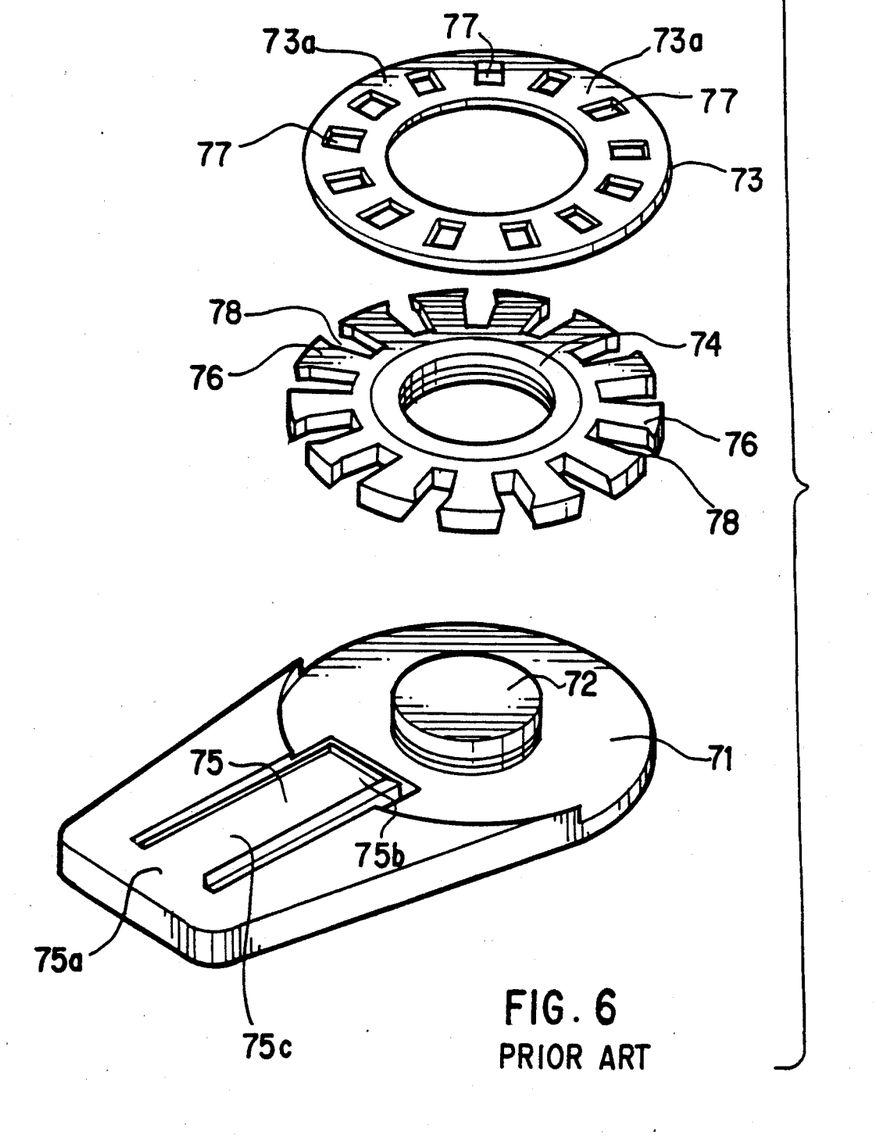
FIG. 6 is an oblique drawing of a comparison device previously proposed by the inventors.

In an effort to solve this problem the inventors have developed the color comparison device shown in FIG. 6, which does not require one to hold the test stick. This device comprises a rotating color sample plate 73 which supports a sample color sheet 73a having multiple color shades positioned circularly about the plate and which is fitted onto a shaft 72 of a fixed circular plate 71 through a rotating plate 74, and a slot section 75 formed on the fixed circular plate 71 for receiving and positioning the color test paper for comparison with the various color shades on sample color sheet 73a.

Slot section 75 is secured at a base end 75a and the other forward end 75b is a free end in relation to the rotational orbit of the rotating plate 74 which fits around the accepting shaft 72. Free end 75b is configured and arranged as an up-down spring which is pushed down by protruding cogs 76 located around the circumference of rotating plate 74.

In between the plurality of adjacent protruding cogs 76 which are used for pushing down the free end 75a of slot section 75 are open sections 78 which are shaped to correspond with window openings 77 of rotating color sample plate 73, and which allow an operator to view a color test paper held on slot section 75 through an aligned open section 78 and a window opening 77.

Figure 7:
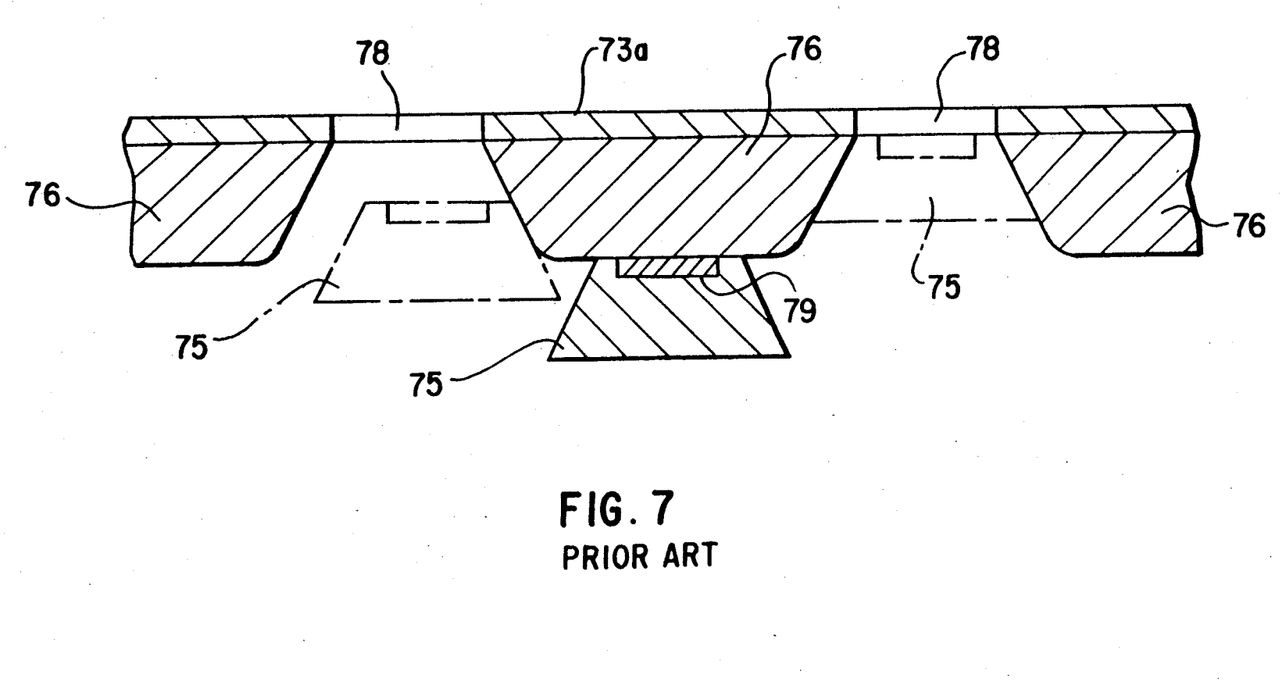
FIG. 7 shown an enlargement of the essential sections of FIG. 6.

To make a color comparison using this color comparison device, a test stick is placed in the slot 75c or slot section 75, and the forward colored end of the color test paper is viewed through an aligned open section 78 and window 77. The rotating plate 74 is then rotated until a color shade on the color sheet 73a which best matches the color of the color test paper is positioned adjacent a window 77 through which the color test paper is viewable. During rotation of plate 74, as shown in FIG. 7, a protruding cog 76 applies a downward force to push slot section 75 down. Further, during rotation of plate 74, after the protruding cog 76 engages with and pushes down on slot section 75, it leaves slot section 75 allowing it to return upwardly by its own resilient bias. At this time, slot section 75 is freed from the downward pressure of the protruding cog 76 and it moves upwardly and between cogs 76. This brings a test paper in slot 75c, through rotation into view through an open section 78 and an aligned window 77. By continuing to rotate the plate 74 in this manner, the color of a color test sample can be successively aligned with the various color shades 73a arrayed in a circular pattern in between windows 77 and compared therewith to determine the same or approximately the same color.

With this type of color comparison device, because a color comparison can be conducted by holding the test stick secure and by rotating the comparative color sample section 73, the color comparison process can be conducted easier and more quickly than with the FIG. 6 comparison device. However, because the FIG. 7 color comparison device produces severe up-down motion of the slot section 75, not only does the support point 75a of the slot have a low reliability, but the up-down drive section requires that the outer shape of the comparison device be relatively large which is disadvantageous.

Thus, an object of this invention is to provide a more reliable test sample color comparison device that can be made smaller and which allows a color comparison operation to be easily and quickly conducted.

SUMMARY OF THE INVENTION

In order to achieve these objectives the test sample color comparison device of this invention comprises a casing unit equipped with an insertion slot for inserting a color test paper from a test sample stick and a display section for successively displaying a plurality of reference color shades adjacent the color test paper to enable a visual color comparison; a manipulable member (preferably a wheel); a comparative color test sample section having multiple color shades positioned in a pattern and which is located on the manipulable member, the manipulable member successively moving the reference color shades to appear in the display section with the color test paper for operator observation; a plurality of convertor switches located in the casing unit in relation to the manipulable member for converting the result of a visually determined color comparison (i.e., the final position of the manipulable member) into an electrical signal, an uneven patterned code section located beneath the manipulable member for operating the converter switches; and a display means for displaying a designated color shade significance in the display section using the electrical signal produced by the convertor switches.

When using a color comparison device constructed as described above to conduct test sample color comparisons, the test stick is first inserted securely into the insertion slot. In this position the color test paper is located so that the reference color shades are located below and on the side of the sample. The manipulable member is then operated to successively bring the various reference color shades into view with the color test paper to allow an operator to determine a best matching color as the manipulable member is moved. In addition, as the manipulable member is moved, the uneven patterned code section on the underside of the manipulable member is also moved, and through this movement, the plurality of convertor switches positioned in relation to the uneven patterned code are turned ON and OFF. The ON and OFF operation of these converter switches forms a multi-bit electric signal that designates that reference color shade which is presently viewed with the color test paper. This electric signal is used to access and display data corresponding to the reference color shade located adjacent the color test paper so that the significance of the adjacent color shade, e.g. a urine sugar level, is displayed in a display section.

As an example of the invention, the reference color comparison sample section can be equipped with 16 color shades and the uneven patterned code section can be equipped with an uneven pattern corresponding to these 16 shades of color. Four independent converter switches are located along the path of movement of the moving uneven pattern which are turned ON and OFF by movement of the uneven pattern. Accordingly, a 4 bit signal is obtained as a result of the respective ON and OFF combinations of the converter switches. Thus the 16 shades of color are designated with four switches. By simply inserting the test stick into the insertion slot and moving the manipulable member in relation to this stationary test stick it is possible to promptly make a color comparison. Furthermore because the platform on which the test stick is placed is not moved up and down, the device can be made smaller and potential fatigue of the hinge point because of up and down movement inherent in the FIG. 6 device is eliminated.

The above and other objects, features and advantages of the invention will be more clearly recognized from the following detailed description of the invention, which is provided in connection with the accompanying drawings.

DETAILED DESCRIPTION OF THE INVENTION

The test sample color comparison device of the invention is illustrated in FIGS. 1-3 and 15. As shown therein it includes a casing unit 1 housing a power source, a CPU (central processing unit) and other electronic circuits; a manipulable wheel 2 that fits onto a protruding display section 11 of casing unit 1, and which has a color sample section 21 on the upper surface thereof and an uneven patterned code section on the underside; and, a cover unit 3 that fits onto casing unit 1.

Figure 2:
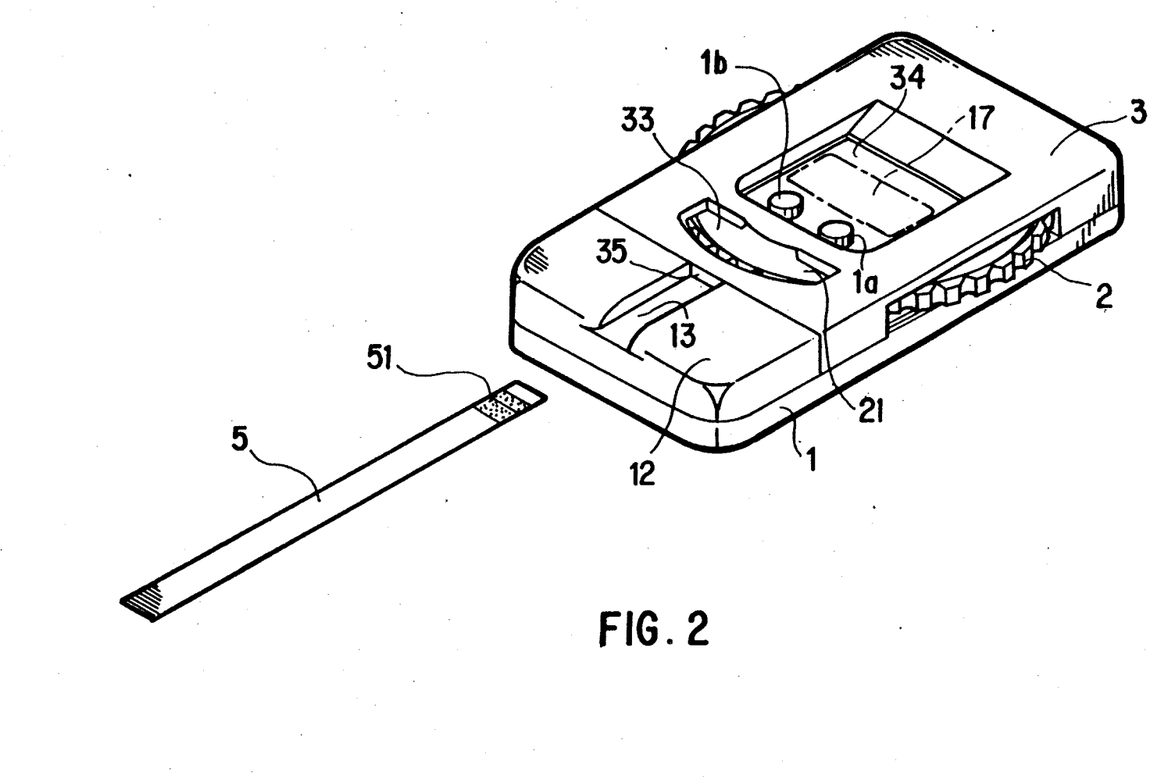
FIG. 2 shows an oblique view of the assembled FIG. 1 embodiment of the color comparison device.

Casing unit 1 has a flat, circular protruding display section 11 in the upper central section, a flat, rectangular protruding platform 12 that thickens towards one edge, and a test stick insertion slot 13 in the central portion of protruding platform 12. Within the surface of this protruding display section 11, is located a display device, for example, an LCD display, a mode key 1a (FIG. 2), and start key 1b (FIG. 2).

Figure 1:
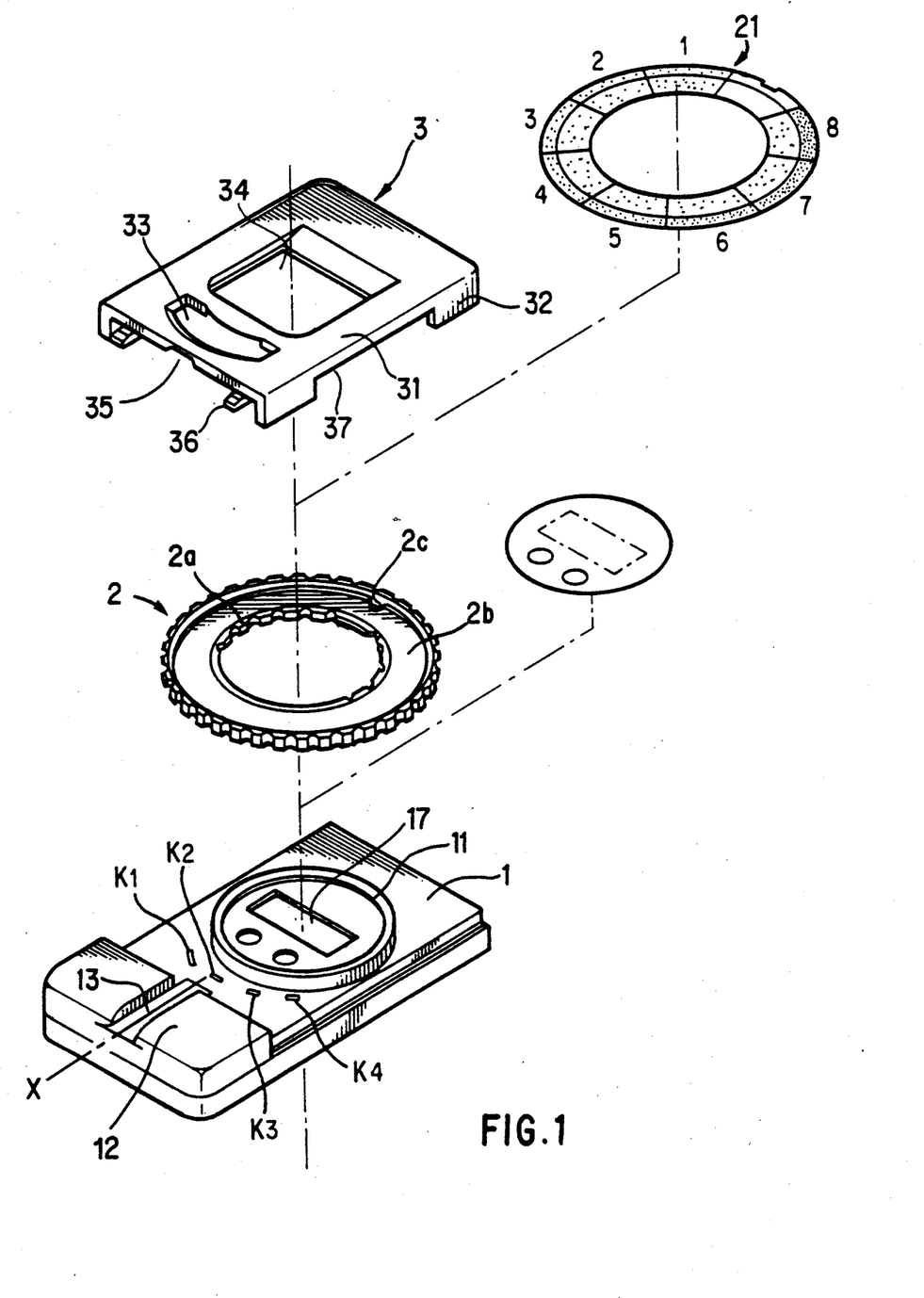
FIG. 1 shows an exploded oblique view of an embodiment of the color comparison device of the invention.
Figure 3:
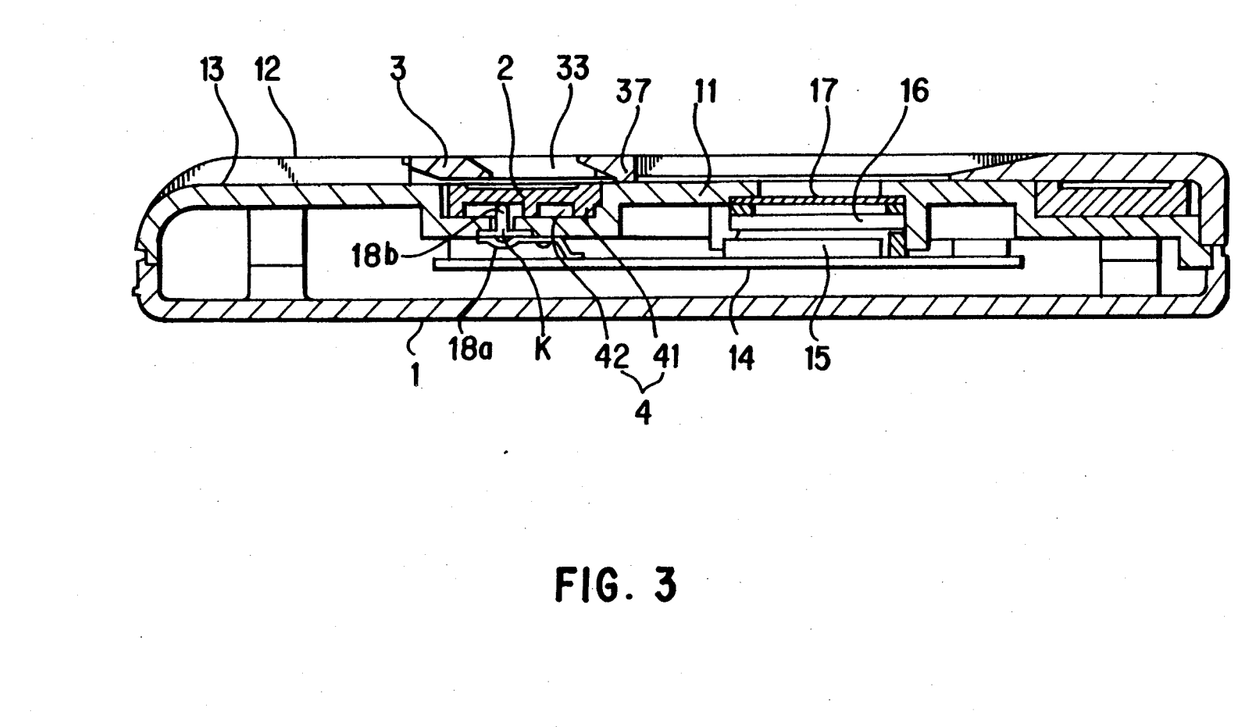
FIG. 3 shows a cross sectional view of the FIG. 1 embodiment of the color comparison device.

An electronic circuit section containing the power source, CPU and other electronics is housed in the central open area of the casing unit 1, as shown in FIG. 3. The electronic circuit section includes circuit board 14, a large scale integrated circuit (LSI) 15 which is located on circuit board 14, a liquid crystal display device (LCD) 16, and a converter switch K. The LSI 15 and LCD 16 (equipped with an LCD cover 17) are located above and below the protruding display section 11. The converter switch K is a four bit switch and is located in between protruding display section 11 and protruding platform 12. Because converter switch K is held in place by one end of a plate spring 18a the other end of which is secured to board 14, the switch head 18b protrudes past the upper wall of the casing unit, in an upward direction, where it is engagable with the uneven pattern code section. The converter switch K converts rotative position of wheel 2 into multi-bit electric signals. Since wheel 2 supports the reference color shades on its upper surface and the uneven pattern code on its lower surface, converter switch K converts the relative position of a reference color shade adjacent a color test sample paper 51, that is, the comparative results of the matching visual comparison between the reference color shades 21 and the color test sample paper 51, into electrical signals. This embodiment, as shown in FIG. 1, has a converter switch K formed by four individual converter switches: $K_1$, $K_2$, $K_3$, and $K_4$. Each switch, $K_1$, $K_2$, $K_3$, and $K_4$ is positioned in circular pattern in relation to the center of the protruding display section 11 in a radial direction at equal intervals, and at equal angles in the circumferential direction. This allows for a 4 bit electrical signal to be obtained. Thus, sixteen reference color shades can be located on the comparison color sample section 21. As described below, the invention uses eight color reference shades and the boundaries between the eight reference shades to form sixteen digitized positions of manipulable wheel 2.

Figure 15:
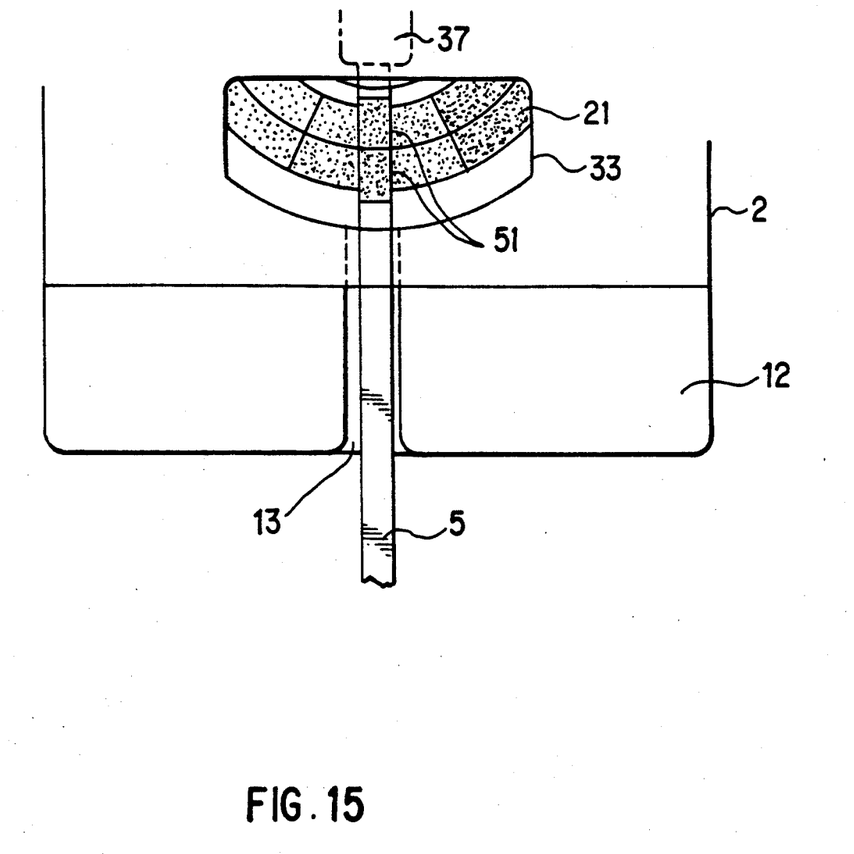
FIG. 15 shows a top view of a portion of the FIG. 1 embodiment.

The manipulable wheel 2 is fitted, so that is can be mounted on and removed from protruding display section 11 and is secured in place by cover unit 3. In the inner circumference of wheel 2 are fifteen grooves 2a, which fit with an indexing portion (not shown) of the outer circumference of protruding display section 11 which allows the wheel to be rotated in increments or stages so that the wheel can be stopped in accurate locations at any stage. On the upper surface of wheel 2 is an indented track which serves as a reference color sample securing groove 2b, and a protrusion 2c which serves to position the color sample section 21 relative to grooves 2a. The comparison color sample section 21 which fits into color sample securing groove 2b is a ring shaped sheet, divided into nine equal sections and of these sections, one does not contain a reference color sample, while the remaining eight sections have eight different reference color shades 1, 2, 3, 4, 5, 6, 7, 8. As illustrated in FIGS. 1 and 15, eight pairs of different color reference shades can be provided for comparison with a pair of test sample colors on test paper 51, shown in FIG. 2.

Figure 4:
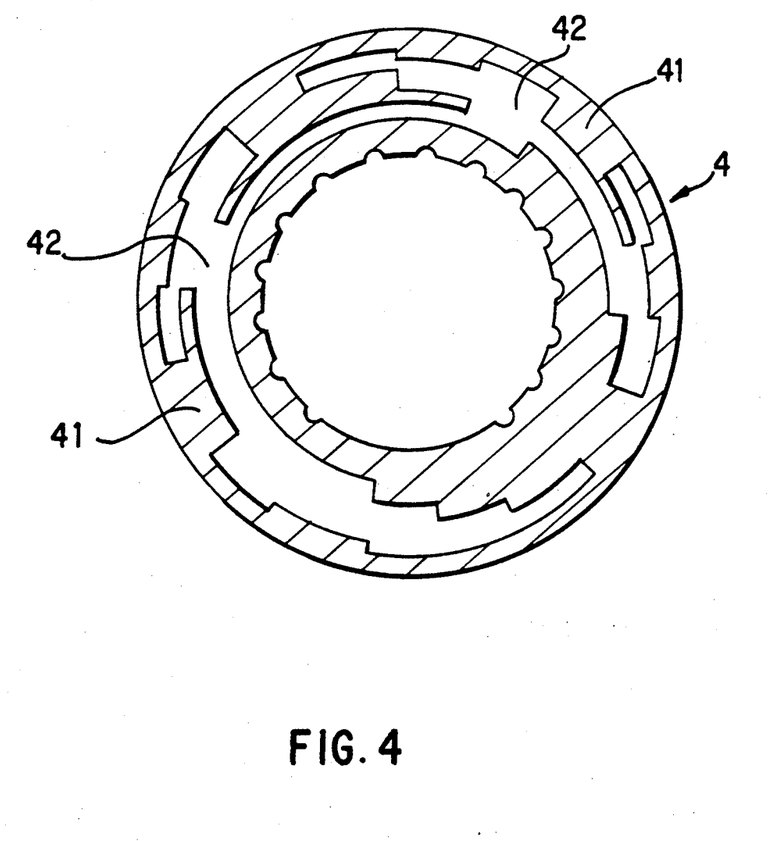
FIG. 4 shows an example of the uneven code section.

The underneath surface of wheel 2, as shown in FIG. 4, forms an uneven pattern code section 4 (FIG. 4) for actuating switches $K_1$, $K_2$, $K_3$ and $K_4$. The uneven pattern of this uneven patterned code section 4 has thick sections 41 and thin sections 42 which are established to correspond to each of the eight reference color shades 1, 2, 3, 4, 5, 6, 7, 8, or comparison color sample section 21. In other words, the uneven patterns are located in a fixed position (angle) relative to each of the color shades and operate the switches $K_1$, $K_2$, $K_3$, and $K_4$. The wheel 2 is indexed to move incrementally in stages so that a central area of each color shade as well as a boundary between two adjacent color shades are positionable to be viewed through display section 33 adjacent a color test paper 51 residing in insertion slot 13 (FIG. 15). The code for that particular color shade or boundary between adjacent shades which is adjacent the color test paper 51 is determined by the relationship of the uneven pattern to the converter switches $K_1$, $K_2$, $K_3$, and $K_4$ which convert the position of wheel 2, and thus the reference color shade or boundary between shades adjacent the test paper, into a 4 bit electric signal.

As shown in FIG. 3, when wheel 2 is rotated, the switches $K_1$, $K_2$, $K_3$, and $K_4$ are pressed down by the corresponding uneven pattern thick sections 41, bringing switch head 4b into contact with board 14, converting the comparison results determined through a visual comparison of color test sample paper 51 and the reference color comparison shades into electrical signals.

Thus, wheel 2 is rotated to select one of the color shades 1, 2, 3, 4, 5, 6, 7, 8, or the boundaries between them which is visually determined to be the closest in color to the color of test sample paper 51. Then start key 1b is pressed and the switches $K_1$, $K_2$, $K_3$, and $K_4$ which are turned ON or OFF by the uneven pattern code section 4 generate a four bit signal which is input to the electronic circuit as a electric signal corresponding to the selected color shade or shade boundary which best corresponds to the color of the test sample paper 51. The shade boundaries are used when the color of the test sheet falls between two reference color shades. The electronic circuit section (CPU) housed within casing unit 1 receives the four bit signal and then displays, on display section 17, the significance of the color shade, for example a read out of a corresponding urine sugar level.

Cover unit 3 is fitted onto casing unit 1 so that it can be mounted and removed. A flange section 32 is located around flat section 31, and this flat section 31 is also equipped with a comparison window 33 through which comparison color sample section 21 and color test sample paper 51 can be simultaneously viewed Flat section 31 also has a manipulable window 34 for viewing protruding display section 11. Further, the end section of cover unit 3 (on the side of comparison window 33) has a test stick insertion slot 35 that connects with the insertion slot section 13. Connecting pieces 36 are located on the side of the cover unit 3 and connect with complementary receptor parts (not shown) in protruding platform 12, allowing cover unit 3 to be fitted and removed from casing unit 1, and when attached, the open section 37 of flange 32 allows the edge of wheel 2 to protrude, permitting wheel 2 to be rotated.

In using a test sample color comparison device having this type of structure when conducting test sample color comparisons, one first pushes mode switch 1a which can be seen in manipulating window 34. Then, when the start switch is pushed after, for example, wetting the test sample paper 51 of test stick 5 with urine, a timer that has been set for a time required for the color reaction starts. When the proper response time has elapsed the timer times out and provides an indication, e.g. an audible sound, thereof to the operator and then the test stick 5 is inserted into insertion slot 13 and appears in comparison window 33 overlying the color sample section 21. The insertion depth of test sample 51 is restricted by stop piece 37 and is stopped at the proper position (FIG. 3). In this position, test sample paper 51 is only slightly above comparative sample color section 21. Manipulable wheel 2 is rotated as an operator compares the color of the test sample paper 51 with the reference color shades on the comparative sample section 21. By rotating wheel 2, the center of each color 1, 2, 3, 4, 5, 6, 7, 8 as well as the borders of the two adjacent colors are brought to the location shown in FIG. 1 as X directly under color test sample paper 51 (see also FIG. 15), and the data for that color shade or border is converted into a 4 bit signal by the switches $K_1$, $K_2$, $K_3$, $K_4$. In other words, the uneven patter (thick and thin sections) 41, 42 of the uneven pattern code section 4 underneath wheel 2, pushes down or does not push down the corresponding converter switches $K_1$, $K_2$, $K_3$, and $K_4$ turning each of the converter switches $K_1$, $K_2$, $K_3$, and $K_4$ either ON or OFF, and converting the results of the visual comparison of color test sample paper 51 and comparative color sample section 21 into electric signals. For example, when the color 3, a shown in FIG. 1, arrives at position X, the uneven pattern on the bottom on wheel 2 turns $K_1$ ON, $K_2$ OFF, $K_3$ ON, and $K_4$ OFF, providing the 4 bit signal "0101" in relation to the on/off states of $K_1$1, $K_2$, $K_3$, and $K_4$. When the boundary between color 3 and 4 arrives at the X position, the signal generated would be "0110." Accordingly, when a color that provides a visual match with color test paper 51, for example, is aligned therewith and start key 1b is depressed ON, the 4 bit data generated by $K_1$, $K_2$, $K_3$, and $K_4$ that indicates the determined color is thereby entered into the CPU and a corresponding urine sugar value is read out by the CPU and displayed on LCD 16.

As is evident from the foregoing, the color test paper section 51 of test stick 5 is simply inserted into insertion slot 13 when comparing colors in order to easily and promptly make a color comparison without requiring the up and down driving mechanism of the insertion slot section 75 in the FIG. 6 comparison device.

In this invention, as described above, a casing unit 3 is provided with an appropriate test stick insertion slot 13, and a manipulable rotating wheel 2 having comparative color sample shades on an upper side and an uneven patterned code section on a lower side that corresponds to the comparative color samples. Switches are provided on the casing for converting the visual comparison results corresponding to the uneven patterned code section into electric signals. By inserting the test stick in the insertion slot and by simply rotating the manipulable wheel it is possible to easily, quickly and reliably display the significance of the designated color arrived at through visual comparison in the display area.

As noted, the pattern code plate 4 (FIG. 4) is constructed of an uneven pattern containing thick sections 41 and thin sections 42 which are located on the underside of wheel 2. Using a 4 bit structure in this example, this uneven pattern is positioned so that it can be moved (can be rotated) over independent multiple converter switches ($K_1$, $K_2$, $K_3$, and $K_4$) which convert a color value to a digital quantity. With the four converter switches ($K_1$, $K_2$, $K_3$, and $K_4$), sixteen incremental movement stages of wheel 2 rotation can be digitized.

Figure 8:
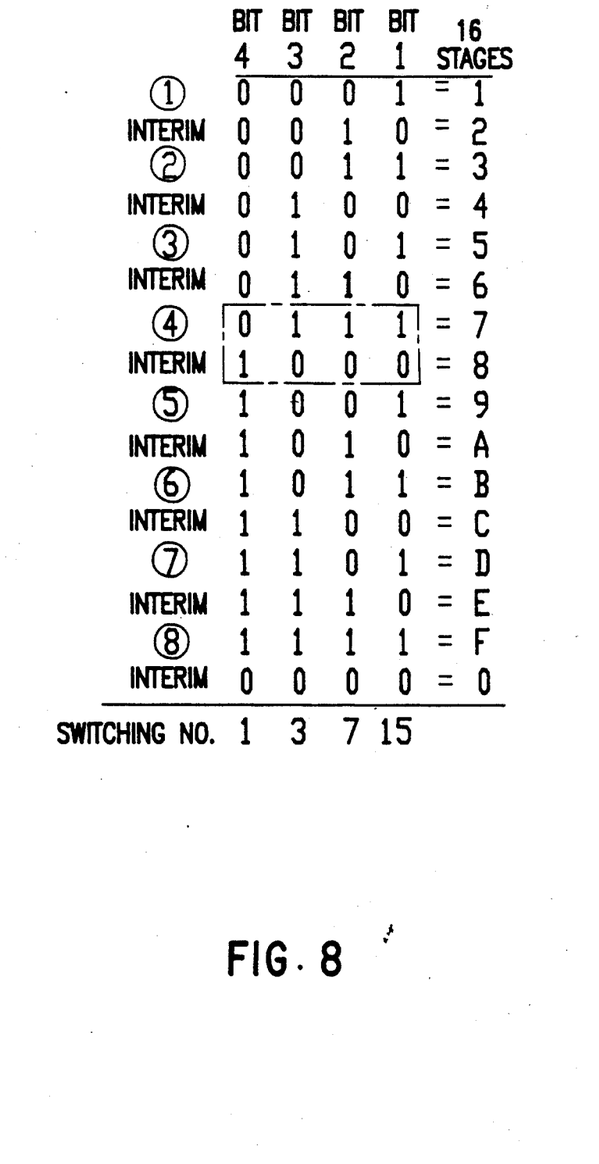
FIG. 8 shows an example of an uneven pattern arrangement for the FIG. 4 uneven code section.

The uneven pattern shown in FIG. 4 is arranged to produce a four bit signal in a regular binary order, from "0" to "F." In other words, the sixteen stages starting with bit 1, bit 2, bit 3, and bit 4, are arranged in order starting from "1" and moving to completion at "F." As a result, when the uneven pattern code plate of FIG. 4 is turned one revolution in relation to converter switches ($K_1$, $K_2$, $K_3$, and $K_4$), there is an imbalance in the number of times each converter switch is switched ON and OFF by the time wheel 2 is rotated through the sixteen stages. For example, bit 1, in other words, the ON-OFF switch $K_1$, is switched fifteen times, bit 2 (switch $K_2$) is switched seven times, bit 3 (switch $K_3$) is switched three times, and bit 4 (switch $K_4$) is switched once. The bit switching pattern for the FIG. 4 code plate is shown in FIG. 8 Thus, there is an extreme imbalance in the number of times each converter switch is switched and switching operations are concentrated only on switch $K_1$. Accordingly, the life span or that switch, which is switched the greatest number of times, is shortened relative to the remaining switches which are switched less frequently.

Further, when rotating the uneven pattern code plate of FIG. 4 through its stages, shown in FIG. 8, when moving from stage 3 to interim (color border) position 3, switches $K_1$ and $K_2$ are switched ON and OFF, while in contrast, when moving from stage 4 to interim (color border) position 4 all switches ($K_1$, $K_2$, $K_3$, $K_4$) are switched ON and OFF. In other words, when rotating the uneven pattern code plate through its stages, a plurality of switches are switched.

Figure 10:
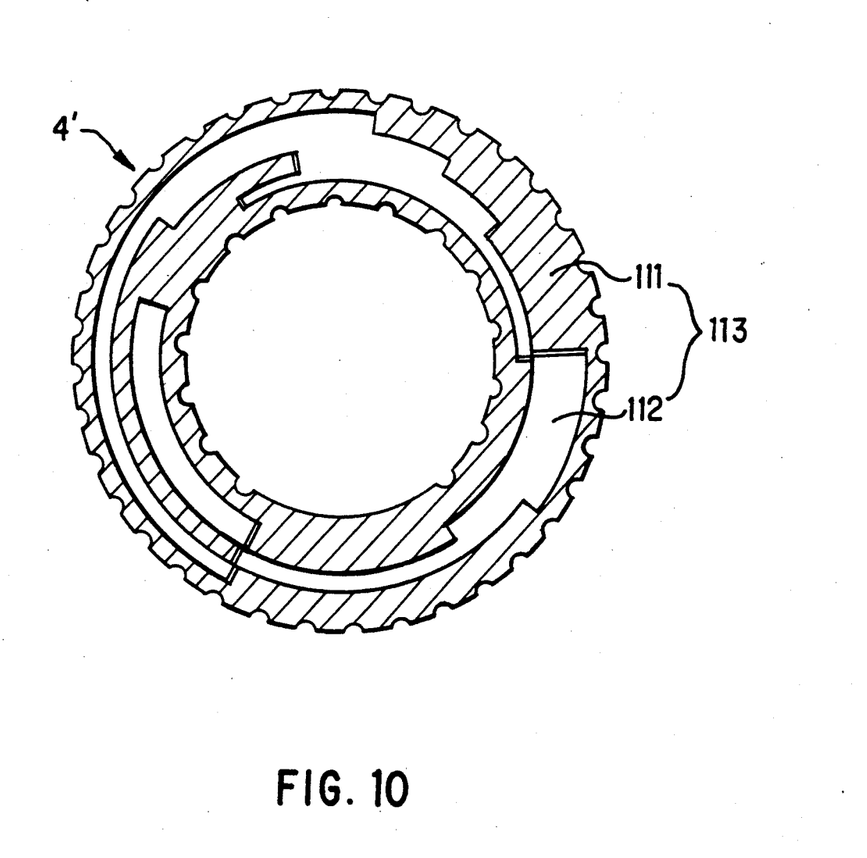
FIG. 10 shows a frontal view of another uneven code plate using the FIG. 9 pattern.

In order to improve upon the FIG. 4 code section, the code section of FIG. 10 has been devised. The FIG. 10 section provides an uneven pattern that uses a low number of converter switch switchings, thereby extending switch life, while providing accurate switch switching.

This uneven pattern code section illustrated in Fig 10 turns movable converter switches ($K_1$, $K_2$, $K_3$, $K_4$) ON and OFF in a manner such that only one of the converter switches is switched during each incremental movement stage of wheel 2, and the number of times each of the converter switches are switched as wheel 2 makes one complete revolution, is set so as to be roughly equal.

With the FIG. 10 code section having the illustrated uneven pattern, the four bit output from switches $K_1$, $K_2$, $K_3$, $K_4$ is not regularly binary ordered from "0" to "F" as in the FIG. 4 code plate, but the order from "0" to "F" varies. When wheel 2 rotates and moves the uneven pattern code plate of FIG. 10 through the sixteen stages, only one of the four convertor switches ($K_1$, $K_2$, $K_3$, $K_4$) is switched during each incremental movement stage and the remaining three are not switched, and when the uneven pattern code plate completes a sixteen stage operation, the number of times the four converter switches ($K_1$, $K_2$, $K_3$, $K_4$) are switched is established so as to be roughly equal.

In addition, since all switching is not concentrated on a single switch, the life of the converter switches is not limited by over use of a single switch, and the life-span of the converter switches as a whole is extended.

The FIG. 10 code section has an uneven pattern 113 which is formed by a combination of thick sections 111 and thin sections 112. The uneven pattern 113 is designed for use in generating a four bit signal, with locations of thick sections 111 and thin sections 112 corresponding to each of the color shades 1, 2, 3, 4, 5, 6, 7, 8. When uneven pattern 113 is at a determined position (angle corresponding to each of the color shades), converter switches $K_1$, $K_2$, $K_3$, $K_4$ are operated. For example, when the central area of each color shade and each color shade boundary, comes into a display position in window 33, the code for that particular color or boundary is determined by the relationship of uneven pattern 113 to converter switches $K_1$, $K_2$, $K_3$, and $K_4$ which produces the four bit electric signal. Thus, when a start key is depressed, the input code for the converter switches $K_1$, $K_2$, $K_3$, $K_4$, turned ON or OFF by the uneven pattern 113, is determined and read out by the electronic circuit section including the CPU housed within casing unit 1. The CPU then displays, on display section 17, the significance of the color shade, for example, it displays a read out of a urine sugar level corresponding to the color shade (or color shade border) which best corresponds to the color of the color test paper 51.

Figure 9:
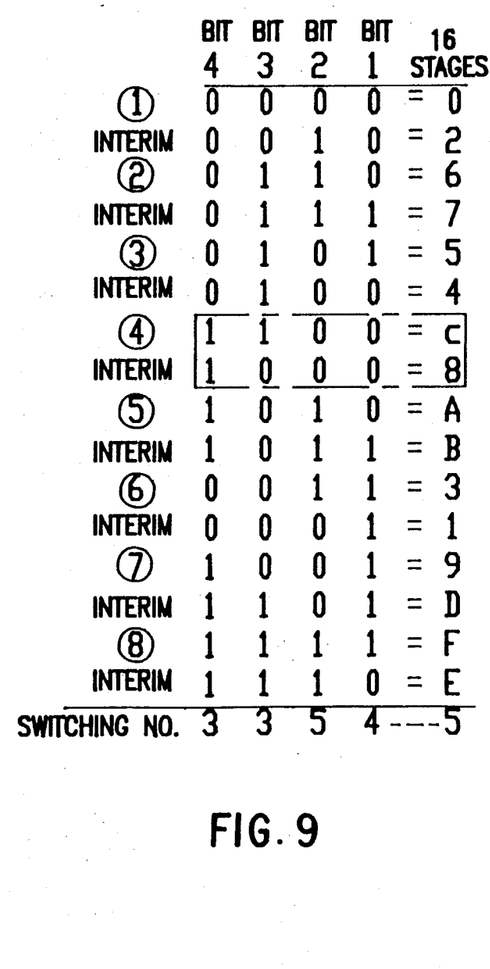
FIG. 9 shows an example of another uneven pattern arrangement for an uneven code section.

With the FIG. 10 code section the four bit pattern does not change in regular binary order but instead the arrayed order of "0" to "F" varies. FIG. 9 shows an example of a four bit array generated by the uneven pattern 113. As shown by FIG. 9, the four bit digital numbers from "0" to "F" are ordered at random. The FIG. 9 arrangement has the following binary signal order: 0, 2, 6, 7, 5, 4, C, 8, A, B, 3, 1, 9, D, F, E.

By arranging the uneven pattern 113 in this way, each time the uneven pattern code plate 2 is moved through each of the sixteen incremental movement stages of wheel 2, in other words, when moved from the stage 1 color to the interim 1 color, only bit 2 (switch $K_2$) is switched ON-OFF, and when moving from the interim 1 color to the stage 2 color, only bit 3, (switch $K_3$) is switched ON-OFF, etc. Thus, when the uneven pattern code section 4 is moved, only one of the four switches $K_1$, $K_2$, $K_3$, $K_4$ is switched, and multiple switches are not switched at the same time. Accordingly, in contrast to the FIG. 4 code section in which when moving from the stage 4 color to the interim 4 color, all four converter switches, $K_1$, $K_2$, $K_3$, $K_4$, were simultaneously switched (FIG. 8); in this example (FIG. 9), even in the case when moving from the stage 4 color to the interim 4 color, only bit 3 (switch $K_3$) is switched ON-OFF, and the other three switches, $K_1$, $K_2$, $K_4$ are not switched ON-OFF. Further, when the uneven pattern code section is moved through all sixteen color stages, namely rotated 360 degrees, bit 1 (switch $K_1$) is switched ON-OFF four times, bit 2 (switch $K_2$) is switched five times, bit 3 (switch $K_3$) is switched three times, and bit 4 (switch $K_4$) is switched three times and each switch ($K_1$, $K_2$, $K_3$, $K_4$) is switched in the range of from three to five times, which is roughly equal. By contrast, the FIG. 4 uneven pattern, as shown in FIG. 8, switches bit 1 (switch $K_1$) fifteen times, bit 2 (switch $K_2$) seven times, bit 3 (switch $K_3$) three times and bit 4 (switch $K_4$) only once, with the result that switching is concentrated on bit 1 (switch $K_1$). Accordingly, the FIG. 10 pattern and FIG. 9 bit array produces a longer life for the switches.

Figure 11:
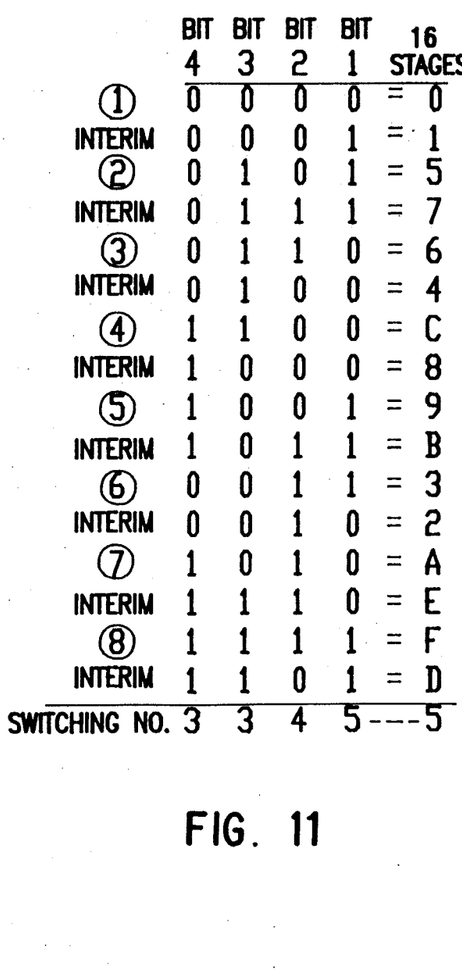
FIG. 11 shown yet another example of another uneven pattern arrangement.
Figure 12:
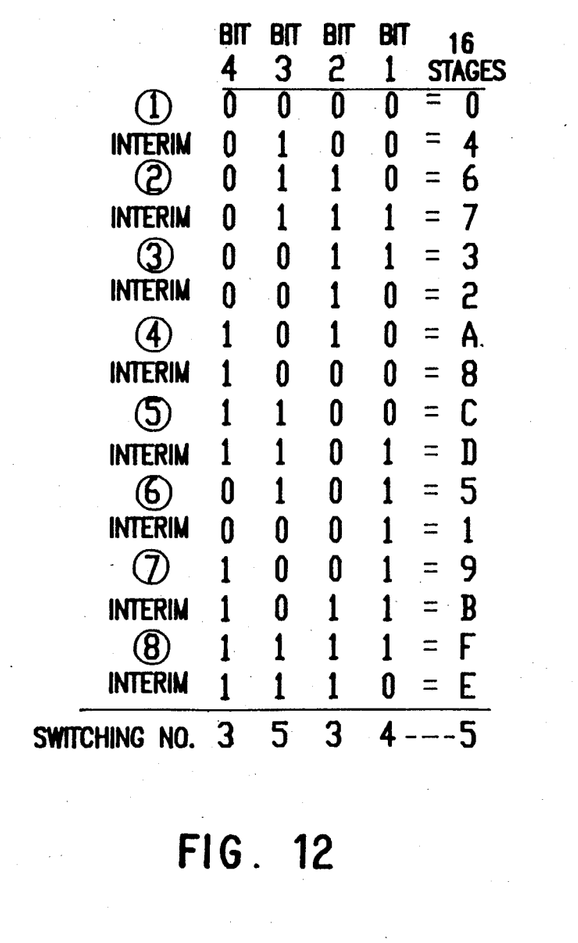
FIG. 12 shows an example of yet another uneven pattern arrangement.
Figure 13:
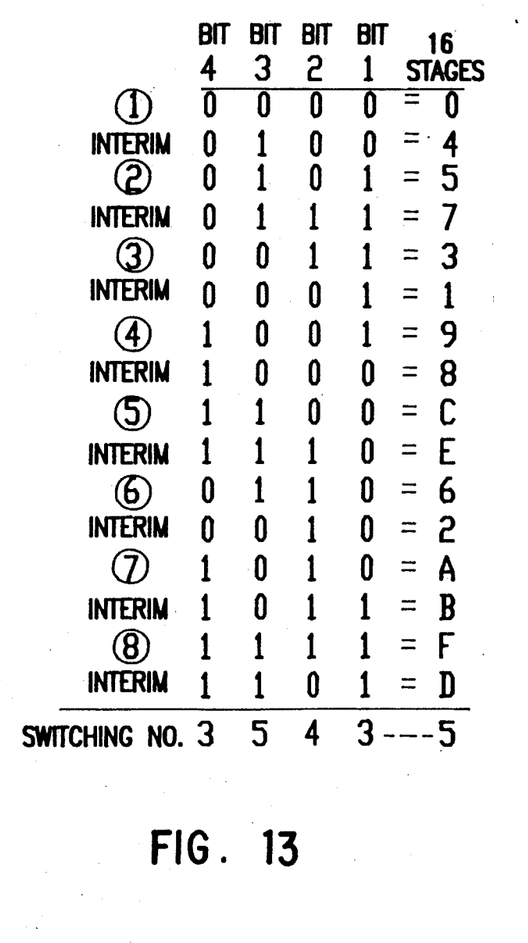
FIG. 13 shows an example of another uneven pattern arrangement.

FIG. 11 through FIG. 13 show other examples of uneven pattern 113 four bit array which produces similar results to the FIG. 9 arrangement. In FIG. 11, FIG. 12, an FIG. 13, as in the case of FIG. 9, when uneven pattern code section 4 is moved through all of the stages, only one of the four switches ($K_1$, $K_2$, $K_3$, $K_4$), are switched ON-OFF at each stage, and the number of times a switch is switched when the uneven pattern code section 4 is moved through all sixteen stages is still in the range from three to five times, i.e. roughly equal.

The example shown in FIG. 9 was devised using on uneven pattern bit arrangement mutually replacing each bit column, and in a similar manner a sixteen section uneven pattern 113 can be obtained. Further if this sixteen section uneven pattern is reversed, a 32 section uneven pattern can be obtained. The examples shown in FIG. 11 through FIG. 13 are presented as other applications of the bit array concept shown in FIG. 9.

Figure 14:
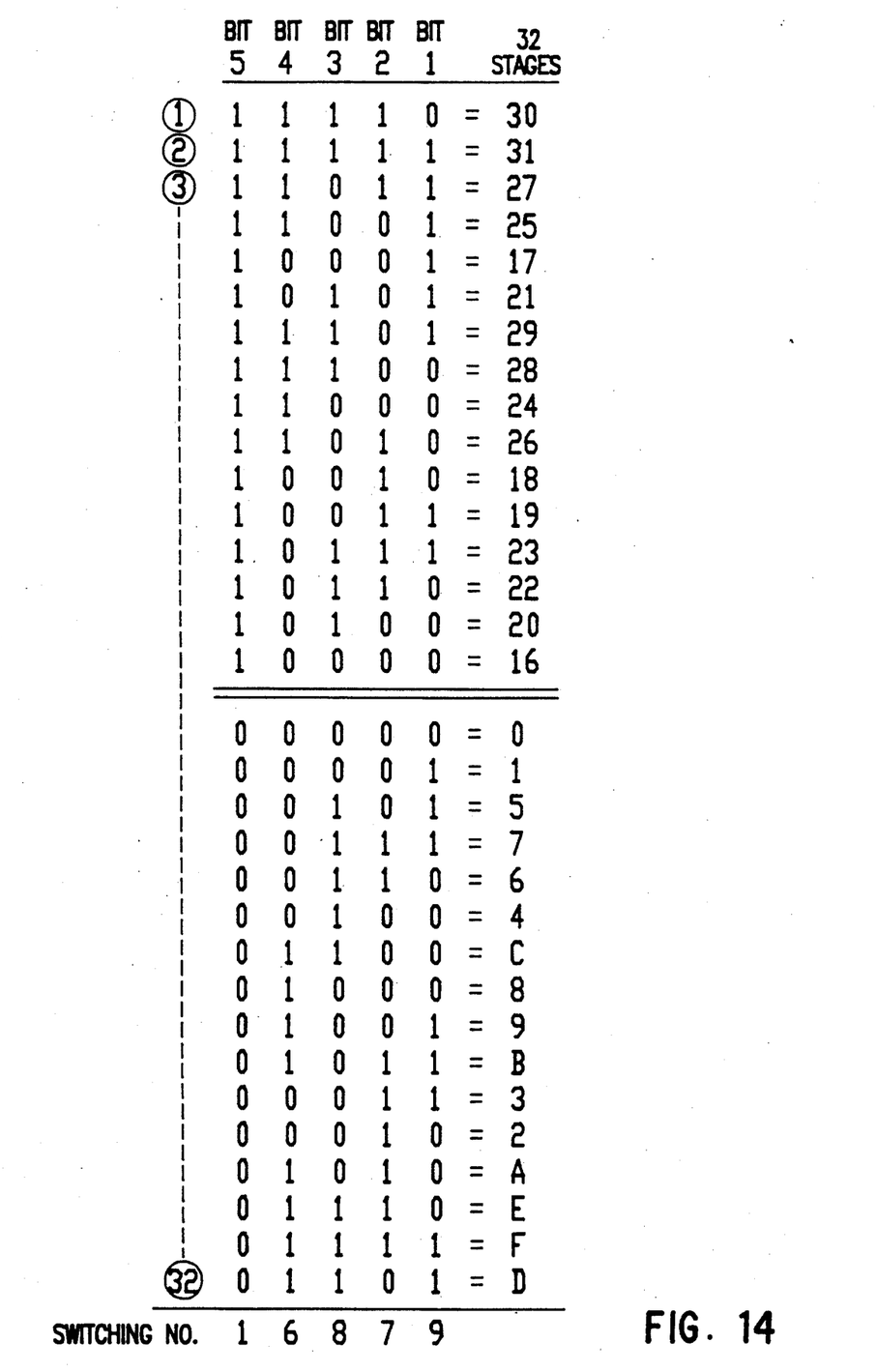
FIG. 14 shows an example of another uneven pattern arrangement.

FIG. 14 shows an example of a 5 bit (32 stage) uneven pattern array. In this example, the 16 section bit arrangement shown in FIG. 11 and the 16 bit arrangement shown in FIG. 12 are combined. In other words, the bit arrangement in FIG. 11 follows the reversed order of the bit arrangement of FIG. 12, and in reversing the bit arrangement of FIG. 12, 1 is added in relation to each of the 16 stages, and 0 is added to each of the 16 stages of the bit arrangement in FIG. 11, to establish 5 bit, or 32 stage designation.

Even in this example, as in the example of FIG. 9 an FIGS. 11 through FIG. 13, when uneven pattern code section 4 is moved through each of the (now 32) stages, only one of the five switches ($K_1$, $K_2$, $K_3$, $K_4$, $K_5$) is switched ON-OFF, and the remaining switches are not affected. further, when the uneven pattern code plate 2 is moved through all 32 stages, bit 1 (switch $K_1$) is switched ON-OFF nine times, bit 2 (switch $K_2$) is switched seven times, bit 3 (switch $K_3$) is switched eight times, bit 4 (switch $K_4$) is switched six times, and bit 5 (switch $K_5$) is switched once. Accordingly, a much lower number of switching times are present than are found, for example, when the bit array shown in FIG. 8 is converted to a 5 bit structure, where bit 1 (switch $K_1$) would then be switched 30 times.

The invention has been described using a rotatable wheel 2 and an uneven pattern code section 4 arranged in a circular shape on the wheel, with the converter switches arranged in relation to the rotation track of the wheel; however, this invention is not limited to this. For example, the movable member and associated uneven pattern code section can be formed in a rectangular shape and moved back and forth directly over the converter switches, with the manipulable member supporting in a linear manner the various reference color shades for comparison with the color test sample paper 51.

Although the invention has been described and illustrated using several representative embodiments, it should be apparent that many changes can be made thereto, without departing from the spirit and scope of the invention. Accordingly, the foregoing description is not to be considered as limiting the scope of the invention. Rather, the invention is only limited by the scope of the appended claims.

We claim:

1. In a test sample color comparison device in which a color of a test sample is compared with a plurality of reference color shades and in which a stored value corresponding to the color shade which best matches the color of the test sample is displayed on a display device the improvement comprising:

a casing unit having an insertion slot for receiving a color test sample, and a display section for viewably displaying a color test sample inserted in said slot along with a succession of reference color shades;

a rotatable wheel having an upper portion;

a comparative color test sample section provided on said upper portion of said wheel and having said succession of reference shades positioned in a pattern forming a circular array of said succession of color shades around an axis of said color wheel, said succession of reference color shades being successively moved into a viewable position adjacent said color test sample in said display section upon rotation of said wheel to thereby permit a visual comparison of said reference color shades with a color of said color test sample through said display section;

switch means for converting the position of said rotatable wheel into an electrical signal representing a position of said comparative color test sample section relative to said color test sample; and an uneven patterned code section movable with movement of said rotatable wheel for operating said switch means.

2. The improvement as in claim 1 wherein said switch means comprises a plurality of on/off switches and said uneven pattern code section operates said switches in accordance with the movement position of said rotatable wheel to produce a multi-bit digital signal representing the position of said color test sample section relative to said color test sample.

3. The improvement as in claim 1 wherein said wheel rotates in incremental stages and wherein said switch means comprises a plurality of converter switches and said uneven patterned code section and said converter switches are arranged and cooperate so that only one converter switch is switched during each incremental movement of said rotatable wheel which positions a next in order color reference shade or a color shade border adjacent said color test sample.

4. The improvement as in claim 3 wherein said uneven patterned code section and said converter switches are arranged and cooperate so that each said converter switch switches states a respective number of times during a complete rotational movement of said rotatable wheel through all its incremental stages and said number of times for any given converter switch is roughly equal to the number of times of ever other converter switch.

5. The improvement as in claim 4 wherein said switch means comprises four converter switches and said respective number of times for each converter switch falls in the range of three to five.

6. The improvement as in claim 1 wherein said wheel rotates in incremental stages and wherein said switch means comprises a plurality of converter switches for generating said electrical signal in the form of a plural bit digital code and said uneven patterned code section and said plurality of converter switches are arranged and cooperate such that as said rotatable wheel is moved through all its incremental stages said converter switches sequentially generate said plural bit digital code in the order of a binary counting sequence.

7. The improvement as in claim 1 wherein said wheel rotates in incremental stages and wherein said switch means comprises a plurality of converter switches for generating said electrical signal in the form of a plural bit digital code and said uneven patterned code section and said plurality of converter switches are arranged and cooperate such that as said rotatable wheel is moved through all its incremental stages said converter switches sequentially generate said plural bit digital code in a different order than an order of a binary counting sequence.

* * * * *